US007033602B1

(12) United States Patent
Pacetti et al.

(10) Patent No.: US 7,033,602 B1
(45) Date of Patent: Apr. 25, 2006

(54) POLYCATIONIC PEPTIDE COATINGS AND METHODS OF COATING IMPLANTABLE MEDICAL DEVICES

(75) Inventors: Stephen D. Pacetti, San Jose, CA (US); Eugene T Michal, San Francisco, CA (US); Syed F A Hossainy, Fremont, CA (US); Ni Ding, San Jose, CA (US); Wouter E Roorda, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 454 days.

(21) Appl. No.: 10/177,116

(22) Filed: Jun. 21, 2002

(51) Int. Cl.
*A61F 2/02* (2006.01)

(52) U.S. Cl. ..................................................... 424/426
(58) Field of Classification Search ................ 424/426
See application file for complete search history.

(56) References Cited

U.S. PATENT DOCUMENTS

| 2,072,303 | A | 3/1937 | Herrmann et al. ........ 128/335.5 |
|---|---|---|---|
| 2,386,454 | A | 10/1945 | Frosch et al. .................. 260/78 |
| 3,773,737 | A | 11/1973 | Goodman et al. ............. 260/78 |
| 3,835,175 | A | 9/1974 | Carpino et al. .............. 260/463 |
| 3,849,514 | A | 11/1974 | Gray, Jr. et al. ............. 260/857 |
| 4,226,243 | A | 10/1980 | Shalaby et al. ........... 128/335.5 |
| 4,329,383 | A | 5/1982 | Joh ............................... 428/36 |
| 4,343,931 | A | 8/1982 | Barrows ..................... 528/291 |
| 4,529,792 | A | 7/1985 | Barrows ..................... 528/291 |
| 4,611,051 | A | 9/1986 | Hayes et al. .............. 528/295.3 |
| 4,656,242 | A | 4/1987 | Swan et al. ............... 528/295.3 |
| 4,733,665 | A | 3/1988 | Palmaz ....................... 128/343 |
| 4,800,882 | A | 1/1989 | Gianturco ................... 128/343 |
| 4,882,168 | A | 11/1989 | Casey et al. ................ 424/468 |
| 4,886,062 | A | 12/1989 | Wiktor ........................ 128/343 |
| 4,908,404 | A | 3/1990 | Benedict et al. .......... 525/54.11 |
| 4,917,309 | A | 4/1990 | Zander et al. .................. 241/5 |
| 4,931,287 | A | 6/1990 | Bae et al. ................... 424/484 |
| 4,941,870 | A | 7/1990 | Okada et al. .................. 600/36 |
| 4,977,901 | A | 12/1990 | Ofstead ....................... 128/772 |
| 5,019,096 | A | 5/1991 | Fox, Jr. et al. ................. 623/1 |
| 5,025,001 | A | 6/1991 | Loscalzo et al. ............. 514/91 |
| 5,100,992 | A | 3/1992 | Cohn et al. ................. 424/501 |
| 5,112,457 | A | 5/1992 | Marchant .................... 204/165 |
| 5,133,742 | A | 7/1992 | Pinchuk ......................... 623/1 |
| 5,155,137 | A | 10/1992 | Keefer et al. ............... 514/611 |
| 5,163,952 | A | 11/1992 | Froix ............................. 623/1 |
| 5,165,919 | A | 11/1992 | Sasaki et al. ............... 424/488 |
| 5,187,183 | A | 2/1993 | Loscalzo et al. ............ 514/400 |
| 5,202,129 | A | 4/1993 | Samejima et al. .......... 424/489 |
| 5,219,980 | A | 6/1993 | Swidler ...................... 528/272 |
| 5,258,020 | A | 11/1993 | Froix ............................. 623/1 |
| 5,272,012 | A | 12/1993 | Opolski ................... 428/423.1 |
| 5,292,516 | A | 3/1994 | Viegas et al. ............... 424/423 |
| 5,298,260 | A | 3/1994 | Viegas et al. ............... 424/486 |
| 5,300,295 | A | 4/1994 | Viegas et al. ............... 424/427 |
| 5,306,501 | A | 4/1994 | Viegas et al. ............... 424/423 |
| 5,306,786 | A | 4/1994 | Moens et al. ............... 525/437 |
| 5,328,471 | A | 7/1994 | Slepian ....................... 604/101 |
| 5,330,768 | A | 7/1994 | Park et al. .................. 424/501 |
| 5,356,890 | A | 10/1994 | Loscalzo et al. ............ 514/210 |
| 5,366,997 | A | 11/1994 | Keefer et al. ............... 614/611 |
| 5,380,299 | A | 1/1995 | Fearnot et al. .............. 604/265 |
| 5,405,919 | A | 4/1995 | Keefer et al. ............... 525/377 |
| 5,417,981 | A | 5/1995 | Endo et al. .................. 424/486 |
| 5,424,077 | A | 6/1995 | Lajoie ......................... 424/641 |
| 5,428,070 | A | 6/1995 | Cooke et al. ................ 514/557 |
| 5,447,724 | A | 9/1995 | Helmus et al. .............. 424/426 |
| 5,455,040 | A | 10/1995 | Marchant .................... 424/426 |
| 5,462,990 | A | 10/1995 | Hubbell et al. ............. 525/54.1 |
| 5,464,650 | A | 11/1995 | Berg et al. ................... 427/2.3 |
| 5,482,720 | A | 1/1996 | Murphy et al. ............. 424/489 |
| 5,485,496 | A | 1/1996 | Lee et al. ...................... 378/64 |
| 5,516,881 | A | 5/1996 | Lee et al. .................... 528/320 |
| 5,536,723 | A | 7/1996 | Loscalzo et al. ............ 514/247 |
| 5,543,099 | A | 8/1996 | Zhang et al. ................ 264/115 |
| 5,569,463 | A | 10/1996 | Helmus et al. .............. 424/426 |
| 5,578,073 | A | 11/1996 | Haimovich et al. ............. 623/1 |
| 5,584,877 | A | 12/1996 | Miyake et al. .................. 623/1 |
| 5,605,696 | A | 2/1997 | Eury et al. .................. 424/423 |
| 5,607,467 | A | 3/1997 | Froix ............................. 623/1 |
| 5,609,629 | A | 3/1997 | Fearnot et al. ................. 623/1 |
| 5,610,241 | A | 3/1997 | Lee et al. .................... 525/411 |
| 5,616,338 | A | 4/1997 | Fox, Jr. et al. .............. 424/423 |
| 5,624,411 | A | 4/1997 | Tuch ........................... 604/265 |
| 5,628,730 | A | 5/1997 | Shapland et al. .............. 604/21 |
| 5,639,441 | A | 6/1997 | Sievers et al. ............... 424/9.3 |
| 5,644,020 | A | 7/1997 | Timmermann et al. ..... 528/288 |
| 5,649,977 | A | 7/1997 | Campbell ...................... 623/1 |
| 5,650,442 | A | 7/1997 | Mitchell et al. ............. 514/611 |

(Continued)

FOREIGN PATENT DOCUMENTS

DE          42 24 401          1/1994

(Continued)

OTHER PUBLICATIONS

Anderson et al., *Nitric-Oxide and Nitrovasodilators: Similarities, Differences and Potential Interactions*, JACC 24(2): 555-566 (1994).

(Continued)

*Primary Examiner*—Carlos A. Azpuru
(74) *Attorney, Agent, or Firm*—Squire, Sanders & Dempsey L.L.P.

(57) ABSTRACT

Coatings for medical devices which include polycationic peptides such as L-arginine and methods for fabricating the coatings are disclosed.

29 Claims, No Drawings

U.S. PATENT DOCUMENTS

| | | | |
|---|---|---|---|
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,804,318 A | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,852,058 A | 12/1998 | Cooke et al. | 514/564 |
| 5,854,376 A | 12/1998 | Higashi | 528/288 |
| 5,858,746 A | 1/1999 | Hubbell et al. | 435/177 |
| 5,861,168 A * | 1/1999 | Cooke et al. | 424/424 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,874,165 A | 2/1999 | Drumheller | 428/308.4 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,891,459 A | 4/1999 | Cooke et al. | 424/439 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,945,452 A | 8/1999 | Cooke et al. | 514/564 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,060,534 A | 5/2000 | Ronan et al. | 523/113 |
| 6,063,432 A | 5/2000 | Maxwell et al. | 426/656 |
| 6,077,543 A | 6/2000 | Gordon et al. | 424/489 |
| 6,080,488 A | 6/2000 | Hostettler et al. | 428/423.3 |
| 6,095,134 A | 8/2000 | Sievers et al. | 128/200.14 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,872 A | 9/2000 | Maxwell et al. | 514/249 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,183,783 B1 | 2/2001 | Benoit et al. | 424/497 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,228,346 B1 | 5/2001 | Zhang et al. | 424/45 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 | 10/2001 | Barry et al. | 623/1.46 |
| 6,306,176 B1 | 10/2001 | Whitbourne | 623/23.59 |
| 6,306,993 B1 | 10/2001 | Rothbard et al. | 526/304 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B1 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B1 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B1 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 514/252.1 |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B1 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |

| | | | |
|---|---|---|---|
| 6,565,659 B1 | 5/2003 | Pacetti et al. ............... 118/500 |
| 6,572,644 B1 | 6/2003 | Moein ...................... 623/1.11 |
| 6,585,755 B1 | 7/2003 | Jackson et al. ............. 623/1.15 |
| 6,585,765 B1 | 7/2003 | Hossainy et al. .......... 623/1.45 |
| 6,585,926 B1 | 7/2003 | Mirzaee ..................... 264/400 |
| 6,605,154 B1 | 8/2003 | Villareal .................... 118/500 |
| 6,616,765 B1 | 9/2003 | Hossaony et al. .......... 623/1.45 |
| 6,623,448 B1 | 9/2003 | Slater ...................... 604/95.01 |
| 6,625,486 B1 | 9/2003 | Lundkvist et al. ............ 604/21 |
| 6,645,135 B1 | 11/2003 | Bhat ............................ 600/3 |
| 6,645,195 B1 | 11/2003 | Bhat et al. .................. 604/528 |
| 6,656,216 B1 | 12/2003 | Hossainy et al. .......... 623/1.13 |
| 6,656,506 B1 | 12/2003 | Wu et al. .................... 424/489 |
| 6,660,034 B1 | 12/2003 | Mandrusov et al. ....... 623/1.42 |
| 6,663,662 B1 | 12/2003 | Pacetti et al. ............... 623/1.13 |
| 6,663,880 B1 | 12/2003 | Roorda et al. ............. 424/423 |
| 6,666,880 B1 | 12/2003 | Chiu et al. .................. 623/1.11 |
| 6,673,154 B1 | 1/2004 | Pacetti et al. ............... 118/500 |
| 6,673,385 B1 | 1/2004 | Ding et al. ................. 427/2.28 |
| 6,689,099 B1 | 2/2004 | Mirzaee ..................... 604/107 |
| 6,695,920 B1 | 2/2004 | Pacetti et al. ............... 118/500 |
| 6,706,013 B1 | 3/2004 | Bhat et al. ................ 604/96.01 |
| 6,709,514 B1 | 3/2004 | Hossainy .................... 118/52 |
| 6,712,845 B1 | 3/2004 | Hossainy .................... 623/1.42 |
| 6,713,119 B1 | 3/2004 | Hossainy et al. ........... 427/2.25 |
| 6,716,444 B1 | 4/2004 | Castro et al. ............... 424/422 |
| 6,723,120 B1 | 4/2004 | Yan ........................... 623/1.15 |
| 6,733,768 B1 | 5/2004 | Hossainy et al. ........... 424/426 |
| 6,740,040 B1 | 5/2004 | Mandrusov et al. ........ 600/439 |
| 6,743,462 B1 | 6/2004 | Pacetti ...................... 427/2.24 |
| 6,746,481 B1 | 6/2004 | Larik et al. |
| 6,749,626 B1 | 6/2004 | Bhat et al. .................. 623/1.1 |
| 6,753,071 B1 | 6/2004 | Pacetti et al. ............... 428/212 |
| 6,758,859 B1 | 7/2004 | Dang et al. ................. 623/1.15 |
| 6,759,054 B1 | 7/2004 | Chen et al. ................. 424/423 |
| 6,764,505 B1 | 7/2004 | Hossainy et al. .......... 623/1.15 |
| 2001/0007083 A1 | 7/2001 | Roorda ...................... 623/1.15 |
| 2001/0014717 A1 | 8/2001 | Hossainy et al. .............. 525/60 |
| 2001/0018469 A1 | 8/2001 | Chen et al. ................. 523/121 |
| 2001/0020011 A1 | 9/2001 | Mathiowitz et al. ......... 514/44 |
| 2001/0029351 A1 | 10/2001 | Falotico et al. ......... 604/103.02 |
| 2001/0037145 A1 | 11/2001 | Guruwaiya et al. ........ 623/1.15 |
| 2001/0051608 A1 | 12/2001 | Mathiowitz et al. ......... 514/44 |
| 2002/0005206 A1 | 1/2002 | Falotico et al. ............. 128/898 |
| 2002/0007213 A1 | 1/2002 | Falotico et al. ............. 623/1.21 |
| 2002/0007214 A1 | 1/2002 | Falotico ..................... 623/1.21 |
| 2002/0007215 A1 | 1/2002 | Falotico et al. ............. 623/1.21 |
| 2002/0009604 A1 | 1/2002 | Zamora et al. ............. 428/450 |
| 2002/0016625 A1 | 2/2002 | Falotico et al. ............. 623/1.13 |
| 2002/0032414 A1 | 3/2002 | Ragheb et al. ............. 604/265 |
| 2002/0032434 A1 | 3/2002 | Chudzik et al. ........... 604/890.1 |
| 2002/0051730 A1 | 5/2002 | Bodnar et al. ................ 422/33 |
| 2002/0071822 A1 | 6/2002 | Uhrich .................... 424/78.37 |
| 2002/0077693 A1 | 6/2002 | Barclay et al. .............. 623/1.13 |
| 2002/0082679 A1 | 6/2002 | Sirhan et al. ............... 623/1.15 |
| 2002/0087123 A1 | 7/2002 | Hossainy et al. ........... 604/198 |
| 2002/0091433 A1 | 7/2002 | Ding et al. .................. 623/1.2 |
| 2002/0094440 A1 | 7/2002 | Llanos et al. ............... 428/424 |
| 2002/0111590 A1 | 8/2002 | Davila et al. ............... 604/265 |
| 2002/0120326 A1 | 8/2002 | Michal ....................... 623/1.15 |
| 2002/0123801 A1 | 9/2002 | Pacetti et al. ............... 623/1.46 |
| 2002/0142039 A1 | 10/2002 | Claude ....................... 424/486 |
| 2002/0155212 A1 | 10/2002 | Hossainy .................... 427/2.25 |
| 2002/0165608 A1 | 11/2002 | Llanos et al. ............... 623/1.45 |
| 2002/0176849 A1 | 11/2002 | Slepian ...................... 424/93.7 |
| 2002/0183581 A1 | 12/2002 | Yoe et al. ...................... 600/3 |
| 2002/0188037 A1 | 12/2002 | Chudzik et al. ............. 523/112 |
| 2002/0188277 A1 | 12/2002 | Roorda et al. ............. 604/523 |
| 2003/0004141 A1 | 1/2003 | Brown ....................... 514/152 |
| 2003/0028243 A1 | 2/2003 | Bates et al. ................. 623/1.15 |
| 2003/0028244 A1 | 2/2003 | Bates et al. ................. 623/1.15 |
| 2003/0031780 A1 | 2/2003 | Chudzik et al. ............. 427/2.1 |
| 2003/0032767 A1 | 2/2003 | Tada et al. .................. 528/310 |
| 2003/0036794 A1 | 2/2003 | Ragheb et al. ............. 623/1.15 |
| 2003/0039689 A1 | 2/2003 | Chen et al. ................. 424/468 |
| 2003/0040712 A1 | 2/2003 | Ray et al. ................... 604/173 |
| 2003/0040790 A1 | 2/2003 | Furst ......................... 623/1.11 |
| 2003/0059520 A1 | 3/2003 | Chen et al. ................. 427/2.1 |
| 2003/0060877 A1 | 3/2003 | Falotico et al. ............. 623/1.42 |
| 2003/0065377 A1 | 4/2003 | Davila et al. ............... 623/1.13 |
| 2003/0072868 A1 | 4/2003 | Harish et al. ............... 427/2.24 |
| 2003/0073961 A1 | 4/2003 | Happ ......................... 604/274 |
| 2003/0083646 A1 | 5/2003 | Sirhan et al. ............. 604/891.1 |
| 2003/0083739 A1 | 5/2003 | Cafferata .................... 623/1.42 |
| 2003/0097088 A1 | 5/2003 | Pacetti ......................... 604/19 |
| 2003/0097173 A1 | 5/2003 | Dutta ......................... 623/1.38 |
| 2003/0099712 A1 | 5/2003 | Jayaraman ................. 424/486 |
| 2003/0105518 A1 | 6/2003 | Dutta ......................... 623/1.38 |
| 2003/0113439 A1 | 6/2003 | Pacetti et al. ............... 427/2.24 |
| 2003/0150380 A1 | 8/2003 | Yoe ........................... 118/423 |
| 2003/0157241 A1 | 8/2003 | Hossainy et al. ........... 427/2.24 |
| 2003/0158517 A1 | 8/2003 | Kokish ................... 604/103.01 |
| 2003/0190406 A1 | 10/2003 | Hossainy et al. ........... 427/2.25 |
| 2003/0207020 A1 | 11/2003 | Villareal .................... 427/2.24 |
| 2003/0211230 A1 | 11/2003 | Pacetti et al. ............... 427/2.24 |
| 2004/0018296 A1 | 1/2004 | Castro et al. ............... 427/2.25 |
| 2004/0029952 A1 | 2/2004 | Chen et al. ................. 514/449 |
| 2004/0047978 A1 | 3/2004 | Hossainy et al. ............. 427/2.1 |
| 2004/0047980 A1 | 3/2004 | Pacetti et al. ............... 427/2.25 |
| 2004/0052858 A1 | 3/2004 | Wu et al. .................... 424/490 |
| 2004/0052859 A1 | 3/2004 | Wu et al. .................... 424/490 |
| 2004/0054104 A1 | 3/2004 | Pacetti ....................... 526/242 |
| 2004/0060508 A1 | 4/2004 | Pacetti et al. ............... 118/264 |
| 2004/0062853 A1 | 4/2004 | Pacetti et al. ............... 427/2.1 |
| 2004/0063805 A1 | 4/2004 | Pacetti et al. ............... 523/113 |
| 2004/0071861 A1 | 4/2004 | Mandrusov et al. ........ 427/2.24 |
| 2004/0072922 A1 | 4/2004 | Hossainy et al. ........... 523/113 |
| 2004/0073298 A1 | 4/2004 | Hossainy ................... 623/1.46 |
| 2004/0086542 A1 | 5/2004 | Hossainy et al. ........... 424/423 |
| 2004/0086550 A1 | 5/2004 | Roorda et al. ............. 424/448 |
| 2004/0096504 A1 | 5/2004 | Michal ....................... 424/471 |
| 2004/0098117 A1 | 5/2004 | Hossainy et al. ........... 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |

| | | |
|---|---|---|
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

Anderson et al., *Close Relation of Endothelial Function in the Human Coronary and Peripheral Circulations*, JACC 26(5):1235-1241 (1995).

Bode-Boger et al., *Elevated L-Arginine/Dimethylarginine Ratio Contributes to Enchanced Systemic NO Production by Dietary L-Arginine in Hypercholesterolemic Rabbits*, Biochem. And Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):1-32 (1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vascu. Biol. 16(1):44-50 (1996).

Chan et al., Asymmetric Dimethylarginine Increases Mononuclear Cell Adhesiveness in Hypercholesterolemic Humans, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis*, Adv. Vasc. Path. 1150:3-14 (1997).

Cooke, *Does ADMA Cause Endothelial Dysfunction?*, Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis an Arginine Deficiency Disease?*, J. Investi. Med. 46(8):377-380 (1998).

Cooke, *Nutriceuticals for Cardiovascular Health*, Am. J. Cardio., 82(10A):43S-46S (1998).

Cooke, *Role of Nitric Oxide in Progression and Regression of Atherosclerosis*, West. J. Med. 164(5):419-424 (1996).

Cooke, *The 1998 Nobel Prize in Medicine: Clinical Implications for 1999 and Beyond*, Vasc. Med. 4:57-60 (1999).

Cooke, *The Endothelium: A New Target for Therapy*, Vasc. Med. 5:49-43 (2000).

Cooke, *The Pathophysiology Of Peripheral Arterial Disease: Rational Targets for Drug Intervention*, Vasc. Med. 2:227-230 (1997).

Creager et al., *L-Arginine Improves Endothelium-Dependent Vasodilation in Hypercholesterolemic Humans*, J. Clin. Investi. 90:1248-1253 (1992).

Drexler et al., *Effect of L-Arginine on Coronary Endothelial Function in Cardiac Transplant Recipients: Relation to Vessel Wall Morphology*, Circ. 89(4):1615-1623 (1994).

Drexler et al., *Endothelial Dysfunction in the Coronary Circulation After Cardiac Transplatation: Effect of L. Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).

http://www.lf2.cuni.dz/physiolres/1997/issues5/iss5cl6. html, Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).

Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).

Ganz et al., *Coronary Vasospasm in Humans—The Role of Atherosclerosis and of Impaired Endothelial Vasodilator Function*, Basic Res. Cardiol. 86(Suppl 2):215-222 (1991).

Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1996).

Gregory et al., *Nitric Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).

Heeschen et al., *Hypercholesterolemia Impairs Angiogenic Response to Hind Limb Ischemia: Role of ADMA* (Abstract 2490), Circ. I-473 (1999).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).

Huet et al., *Structural Homologies Between Two HLA B27-Restricted Peptides Suggest Residues Important for Interaction with HLA B27*, Intl. Immunol. 2(4):311-316 (1990).

Hutchison et al., *Effects of L-Arginine on Atherogenesis and Endothelial Dysfunction Due to Secondhand Smoke*, Hyperten. 34:44-50 (1998).

Jang et al., *Angiogenesis is Impaired by Hypercholesterolemia: Role of Asymmetric Dimethylarginine*, Circ. 102:1414-1419 (2000).

Jang et al., *L-Arginine Reverses the Anti-Angiogenic Effects of Asymmetric Dimethylarginine* (Abstract), J. Investi. Med. 4(2):86A (1999).

Jozkowicz et al., *Genetic Augmentation of Nitric Oxide Synthase Increases the Vascular Generation of VEGF*, Cardiovasc. Res. 51:773-783 (2001).

Kown et al., *Arginine Polymers Inhibit Graft Coronary Artery Diseases Following Cardiac Transplantation* (Abstract 726), Transplant. 69(8):S300 (2000).

Kown et al., *L-Arginine Polymers Inhibit the Development of Vein Graft Neointimal Hyperplasia*, J. Thorac. Cardiovasc. Surg. 121(5):971-980 (2001).

Kown et al., *L-Arginine Polymer Mediated Inhibition of Graft Coronary Artery Disease After Cardiac Transplantation*, Transplant. 71(11):1542-1548 (2001).

Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).

Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).

Kyte et al., *A Simple Method for Displaying the Hydropathic Character of a Protein*, J. Mol. Biol. 157:105-132 (1982).

Latron et al., *Positioning of a Peptide in the Cleft of HLA-A2 by Complementing Amino Acid Changes*, PNAS 88:11325-11329 (1991).

Lieberman et al., *Estrogen Improves Endothelium-Dependent, Flow-Mediated Vasodilation in Postmenopausal Women*, Annals Intern. Med. 121(12):936-941 (1994).

Lieberman et al., *Flow-Induced Vasodilation of the Human Brachial Artery is Imparied in Patients <40 Years of Age with Coronary Artery Disease*, Am. J. Cardiol. 78:1210-1214 (1996).

Lim et al., *Acute Local Delivery of L-Arginine Reduces Long Term Intimal Thickening and Macrophage Infiltration* (Abstract 2346), Circ. 94(8):1403 (1996).

Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).

Lissin et al., *Maintaining the Endothelium: Preventive Strategies for Vessel Integrity*, Prev. Cardio. 3:172-177 (2000).

Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).

Maxwell et al., *A Nutritional Product Designed to Enhance Nitric Oxide Activity Restores Endothelium-Dependent Function in Hypercholesterolemia*, J. Investi, Med. 47(2): 45A (1999).

Maxwell et al., *Cardiovascular Effects of L-Arginine*, Curr. Opin. Nephrol. Hyperten. 7:63-70 (1998).

Maxwell et al., *Endothelial Dysfunction in Hypercholesterolemia is Reversed by a Nutritional Product Designed to Enhance Nitric Oxide Activity*, Cardiovasc. Drugs Therapy 14:309-316 (2000).

Maxwell et al., *Improvement in Walking Distance and Quality of Life in Peripheral Arterial Disease by a Medical Food* (Abstract 86), Nitric Oxide: Biology and Chemistry, 4(3): 232 (2000).

Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercise Capacity in Association with Augmented Nitric Oxide Production*, J. Appl. Physiol. 90:933-938 (2001).

Maxwell et al., *Limb Blood Flow During Exercise is Dependent on Nitric Oxide*, Circ. 98:369-374 (1998).

Maxwell et al., *Modulation of the Nitric Oxide Synthase Pathway in Atherosclerosis*, Exp. Physiol. 83:573-584 (1998).

Maxwell et al., *Nutritional Therapy for Peripheral Arterial Disease: A Double-Blind, Placebo-Controlled, Randomized Trial of HeartBar®*, Vasc. Med. 5:11-19 (2000).

Maxwell et al., *The Role of Nitric Oxide in Atherosclerosis*, Cor. Art. Dis. 10:277-286 (1999).

Meredith et al., *Role of Endothelium in Ischemic Coronary Syndromes*, Am. J. Cardiol. 72(8):27C-32C (1993).

Meredith et al., *Role of Impaired Endothelium-Dependent Vasodilation in Ischemic Manifestations of Coronary Artery Disease*, Circ. 87(5) Suppl:V56-V66 (1993).

Mitchell et al.; *Polyarginine Enters Cells More Efficiently than Other Polycationic Homopolymers*, J. Peptide Res. 56:318-325 (2000).

Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate In The Absence Of Changes In Arterial Blood Pressure When Applied Topically To The Sino-Atrial Node In The Anaesthetized Pig*, J. Physiol. (2000), printed Jun. 12, 2001.

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone in vivo Using Intravascular Ultrasound*, J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity in vivo*, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., Altered Reactivity of the Inferior Vena Cava to Noradrenaline and Acetylcholine Following the Blockade of EDRF-Biosynthesis with $N^G$Nitro-$_L$-Arginine Methyl Ester, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci. org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract I20), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Alter Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and The Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by The NO Precursor* (Abstract 765-4), JACC 25:276A (1995).

Todd et al., *Regulation of Loblolly Pine* (Pinus taeda L.) *Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enchanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion:* in vivo *Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase As an* in vivo *Gene Transfer Approach to Prevent Neointima Formation After Vascular Injury*, Clin. Res. 42(22):180A (1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine In Cardiovascular Health*, U.S. Pharmacist Continuing Education, printed Sep. 12, 2002.

U.S. Appl. No. 10/177,156, filed Jun. 21, 2002, Michal et al.

U.S. Appl. No. 10/176,499, filed Jun. 21, 2002, Hossainy et al.

Anonymous, Reducing the pH of a peptide oligomer to prepare for systemic delivery, Defensive Publication, Research Disclosure, p. 905 (Aug. 2003).

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

Anonymous, *Harparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/ cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Gentically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnical. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrics Containing Anticancer Agents on Ehrlich Ascites Carcinoma and P388 Leukemia in Mice*, Chem. Pharm. Bull. 33(6) 2490-2498 (1985).

Miyazawa et al., *Effects of Permirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

POLYCATIONIC PEPTIDE COATINGS AND METHODS OF COATING IMPLANTABLE MEDICAL DEVICES

BACKGROUND OF THE INVENTION

1. Field of the Invention

This invention relates to the field of medical devices, such as stents. More particularly, this invention is directed to coatings which include polycationic peptides such as polymers and/or oligomers of L-arginine.

2. Description of the State of the Art

In the field of medical technology, there is frequently a necessity to administer a therapeutic substance locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results. For the treatment of vascular occlusions, such as restenosis, stents are being modified to administer therapeutic substances locally. One method of medicating a stent is with the use of a polymer coating impregnated with a therapeutic substance. The coating allows for the sustained release of the substance at the treatment site. L-arginine, or polypeptide oligomeric derivatives or analogs thereof, for example, those containing 5 to 20 amino acid units are one example of a therapeutic substance that can be used in conjunction with a stent.

L-arginine is a known precursor of endothelium derived nitric oxide (NO). NO is synthesized from L-arginine, or its polymeric and/or oligomeric derivatives, by the enzyme NO synthase oxygenase, a homodimeric flavo-hemoprotein that catalyzes the 5-electron oxidation of L-arginine to produce NO and L-citrulline. Among other therapeutic properties, NO regulates vascular tone, inhibits platelet aggregation, and inhibits vascular smooth muscle proliferation. These therapeutic properties are believed to contribute to the reduction or elimination of neointimal hyperplasia in vascular injury models.

U.S. Pat. No. 5,861,168 to Cooke et al. teaches that NO activity is reduced after vascular injury. Cooke et al. also teach that administering L-arginine as the NO precursor helps to restore vascular NO activity in patients with endothelial vasodilator dysfunction due to restenosis. It has been also taught that oligomeric peptides comprising 6 to 15 units of L- or D-arginine can be effective transfectors of cells (see, Mitchell, et al., *J. Peptide Res.*, vol. 56, p. 318 (2000)) and, using a rabbit vein-graft model, it has been demonstrated that oligomers of L- or D-arginine can inhibit vascular smooth cell proliferation by efficiently transfecting cells. See, Uemura, et al., *Circulation*, vol. 102, p. 2629 (2000). Using the rabbit model, it has also been shown that intramural administration of L-arginine inhibits lesion formation in a hypercholesterolemic balloon injury. See, Schwarzacher et al. *Circulation*, vol. 95, p. 1863 (1997).

Due to the strong basicity of the guanidinium group, —NH—C(NH$_2$)=NH, L-arginine is highly cationic. For example, the heptamer of L-arginine has the pK$_a$=13.2. This high degree of polarity causes L-arginine, or its polymers and/or oligomers, to be practically insoluble in most organic solvents having the Hildebrand solubility parameter $\delta \leq 12.7$ (cal/cm$^3$)$^{1/2}$.

The term "Hildebrand solubility parameter" refers to a parameter measuring the cohesion of a substance. The δ parameter is determined as follows:

$$\delta = (\Delta E/V)^{1/2}$$

where
  δ=solubility parameter, (cal/cm$^3$)$^{1/2}$;
  ΔE=energy of vaporization, cal;
  V=molar volume, cm$^3$ The more polar the solvent, the higher its cohesion due to the existence of strong van der Waals forces. Consequently, it takes more energy to vaporize more polar substances, resulting in the higher numerical value of δ.

Thus, L-arginine or its polymers and/or oligomers are believed to be soluble only in water (δ=23.4 (cal/cm$^3$)$^{1/2}$)(as much as 15% by weight concentration in water can be achieved for the heptamer of L-arginine) and have some limited solubility only in very polar solvents having high values of δ, for example, formamide (δ=19.2 (cal/cm$^3$)$^{1/2}$), methanol (δ=14.5(cal/cm$^3$)$^{1/2}$), or ethanol (δ=12.7 (cal/cm$^3$)$^{1/2}$).

While polycationic peptides, such as L-arginine, are practically not soluble in many organic solvents, the polymers from which the stent coatings are made are soluble in organic solvents but not water. The incompatibility of solubility of the polymer and L-arginine in a common solvent or common mixture of solvents can lead to poor coating characteristics and poor release profile of the peptide from the coating. Furthermore, the high degree of solubility of polycationic peptides in water tends to increase the in vivo rate of release of the peptides, which may be undesirable. Polycationic peptides are essentially incompatible with hydrophobic polymers which are commonly used to coat a stent. The embodiments of the present invention address these and other deficiencies.

SUMMARY

According to one embodiment of this invention, a therapeutic composition is provided, the composition comprises a polycationic peptide and a hydrophobic counter-ion coordinated with the polycationic peptide. The polycationic peptide can include poly(L-arginine), poly(D-arginine), poly(D,L-arginine), poly(L-lysine), poly(D-lysine), poly(δ-guanidino-α-aminobutyric acid), and a racemic mixture of poly(L-arginine) or poly(D-arginine). The hydrophobic counter-ion can be derived from saturated fatty acids, unsaturated fatty acids, phoshpolipids, sulfates, aromatic compounds or hydrophobic anionic compounds.

According to another embodiment of this invention, a method for making a polycationic peptide soluble in an organic solvent is provided, the method comprises preparing a complex of the peptide with a hydrophobic counter-ion. The complex can be prepared by a free base method, a dialysis method, an ion exchange method, a selective precipitation method, or a volatilization method.

According to yet another embodiment of this invention, a coating for an implantable device is provided, the coating comprises a polycationic peptide and a hydrophobic counter-ion coordinated with the polycationic peptide.

According to yet another embodiment of the present invention, a coating for an implantable medical device is provided, the coating comprises a polymer and a complex comprising a polycationic peptide and a counter-ion, wherein the complex is bonded to the polymer. The polymer can include hydroxyl, glycidyl, amino, carboxyl, or aldehyde functional groups, or a combination thereof.

According to yet another embodiment of this invention, a method of coating an implantable medical device is provided, the method comprises applying a polymer composition onto the device, and bonding an anionic polysaccharide-peptide complex to the polymer. The anionic polysaccharide can include heparin, heparin salts, heparinoids, dermatan sulfate, keratan sulfate, chondroitin sulfate, hyaluronic acid, hyaluronates, and mixtures thereof.

According to yet another embodiment of the present invention, a method of coating an implantable medical device with a polymer composition comprising a polycationic peptide is provided, the method comprises applying onto the device an organic solvent solution comprising a complex of the peptide with a hydrophobic counter-ion to form the coating and heat-treating the coating. The hydrophobic counter-ion can be derived from formic acid or acetic acid.

According to another embodiment of this invention, a method of coating an implantable medical device is provided, the method comprises incorporating a polycationic peptide into microspheres, adding the microspheres to a composition including a polymer, and applying the composition to the device.

According to yet another embodiment of the present invention, a coating for an implantable medical device is provided, the coating comprises a hydrogel polymer and a polycationic peptide incorporated into the hydrogel polymer. The polycationic peptide can include poly(L-arginine), poly(D-arginine), poly(D,L-arginine), poly(L-lysine), poly(D-lysine), poly(δ-guanidino-α-aminobutyric acid), and a racemic mixture of poly(L-arginine) or poly(D-arginine), and the hydrogel polymer is made by homopolymerization or copolymerization of one or plurality of acrylate, methacrylate, allyl or vinyl monomers and/or oligomers.

According to another embodiment of this invention, a coating for an implantable medical device is provided, the coating comprises a polycationic polyelectrolyte and a polyanionic polyelectrolyte.

According to another embodiment of this invention, a method for coating an implantable medical device is provided, the method comprises applying alternating layers of a polycationic polyelectrolyte and a polyanionic polyelectrolyte onto the device. The polycationic polyelectrolyte can include poly(L-arginine), poly(D-arginine), poly(D,L-arginine), poly(L-lysine), poly(D-lysine), poly(δ-guanidino-α-aminobutyric acid), and a racemic mixture of poly(L-arginine), poly(D-arginine), chitosan, or a mixture thereof, and the polyanionic polyelectrolyte includes heparin, derivatives of heparin, oligonucleotides, RNA, chondroitin sulfate, dextran sulfate, hyaluronic acid, hyaluronates, carboxymethyl cellulose, poly(acrylic acid), poly(methacrylic acid), poly(ethyl acrylic acid), poly(propyl acrylic acid), poly(ethylene-co-acrylic acid), poly(ethylene-co-methacrylic acid), or a mixture thereof.

DETAILED DESCRIPTION

L-arginine, also known as 2-amino-5-guanidinovaleric acid, is an amino acid having a formula $NH=C(NH_2)-NH-CH_2-CH_2-CH_2-CH(NH_2)-COOH$. Polymers and/or oligomers of L-arginine that can be used are referred to herein as "PArg" and comprise a plurality of repeating monomeric amino acid units connected with peptide bonds. PArg has a general formula $H[NH-CHX-CO]_p-OH$, where "p" can be within a range of 5 and 1,000, typically, within a range of between 6 and 20. For example, a heptamer (designated R7), having p=7, can be used.

In the formula of PArg, "X" is a 1-guanidinopropyl radical having the chemical structure $-CH_2-CH_2-CH_2-NH-C(NH_2)=NH$. The terms "polymers and/or oligomers of L-arginine," "poly-L-arginine," and "PArg" are intended to include L-arginine in both its polymeric and oligomeric form. Representative examples of these polycationic peptides include poly(L-arginine), poly(D-arginine), poly(D,L-arginine), poly(L-lysine), poly(D-lysine), poly(δ-guanidino-α-aminobutyric acid), racemic mixtures of poly(L-arginine) and poly(D-arginine), and chitosan.

A. Achieving Solubility of PArg in Organic Solvents by Coordinating PArg with Hydrophobic Counter-Ions In one embodiment for achieving solubility of PArg in an organic solvent, PArg is coordinated with hydrophobic counter-ions. The hydrophobic counter-ions with which PArg and other suitable polypeptides can be coordinated include anions $Z-COO^-$ of the following saturated fatty acids $Z-COOH$: formic ($Z=H$), acetic ($Z=CH_3$), propionic ($Z=C_2H_5$), butyric ($Z=C_3H_7$), valeric ($Z=C_4H_9$), caproic ($Z=C_5H_{11}$), enanthic ($Z=C_6H_{13}$), caprylic ($Z=C_7H_{15}$), pelargonic ($Z=C_8H_{17}$), capric ($Z=C_9H_{19}$), hendecanoic ($Z=C_{10}H_{21}$), lauric ($Z=C_{11}H_{23}$), myristic ($Z=C_{13}H_{27}$), palmitic ($Z=C_{15}H_{31}$), stearic ($Z=C_{17}H_{35}$), and arachidic ($Z=C_{19}H_{39}$). The anions can be derived from the acids themselves or from their salts, for example, from sodium salts $ZCOO^-Na^+$.

The hydrophobic counter-ions with which PArg and other suitable polypeptides can be coordinated also include anions $Z'-COO^-$ of the following unsaturated fatty acids $Z'-COOH$: palmitoleic ($Z'=C_{15}H_{29}$), oleic ($Z'=C_{17}H_{33}$), linoleic ($Z'=C_{17}H_{31}$), arachidonic ($Z'=C_{19}H_{31}$), or from salts thereof, for example, from sodium salts $Z'COO^-Na^+$.

Other compounds that can be used to generate acceptable hydrophobic counter-ions with which PArg and other suitable polypeptides can be coordinated include phoshpolipids, for example, phosphatidic acids, phosphatidylinositol, phosphatidylglycerol, diphosphatidylglycerol, or salts thereof; sulfates, for example, sodium dodecyl sulfate; and aromatic compounds, for example, benzoic acid, salicylic acid, acetyl salicylic acid (known as aspirin) and aromatic sulfonates, and anionic biologically active compounds. Examples of such suitable hydrophobic anionic biologically active compounds include statins, retinoic acid and retinoids. The hydrophobic counter-ions that can be used are herein designated as $AN^-$.

PArg such as R7 is commonly produced by peptide synthesis. The synthesis is known to those having ordinary skill in the art. At the end of the peptide synthesis, R7 is cleaved off the support resin, usually with trifluoroacetic acid (TFA) or trifluoromethane sulfonic acid. The hydrophobic counter-ion, such as one of the counter-ions $AN^-$ described above, is then coordinated with R7 using one of the following methods.

1. Free Base Method.

The free base method is directed to formation of the free base of R7. R7 can be dissolved in water and a strong alkali can be added, such as potassium hydroxide KOH, so as to create a homogeneous basic solution. The pH of the R7 solution (solution I) in water can be typically raised to about 13. In such a strongly alkaline environment, the guanidinium side branches of R7 are de-protonated and R7 in a free base form can be obtained as a result. In the free base form, R7 has only one charged group, an anionic carboxyl at one terminus. The guanidinium side groups are neutral. For the purposes of this invention, R7 in the free base form is designated as R7-FB.

One of the above-identified substances forming hydrophobic counter-ions $AN^-$, or a mixture of such substances, can be dissolved in an appropriate organic solvent, such as toluene, methylene chloride, octanol, cyclohexane, chloroform, or diethyl ether (solution II). R7-FB obtained as described above can then be extracted into solution II by blending and vigorously shaking the free base aqueous solution I and solution II.

As a result of the extraction, R7-FB will migrate into the organic solution. The hydrophobic counter-ions in the form of the free acid will also remain in the organic phase. If a stoichiometric amount of KOH is used to make the R7-FB, the R7-FB will both migrate into the organic phase and undergo an acid-base reaction forming a $R7^+/AN^-$ complex that is soluble in the organic phase. After separating the organic phase from the aqueous phase, the complex can then be isolated from the organic phase by evaporating the solvent, cooling the solution, or precipitating by a compound which is a non-solvent for the complex.

2. Dialysis Method.

According to this method, an aqueous solution of $R7^+$ in the free base form can be made as described above. The R7 solution can be dialyzed using standard techniques known to those having ordinary skill in the art. Typically, a dialysis membrane having a molecular weight cutoff of about 1,000 can be used for the R7 solution. The purpose of the dialysis is to remove the counter-ions that were originally with R7, such as trifluoro acetate. If desired, the progress of the dialysis can be monitored by measuring the conductivity of the R7 solution.

Once the aqueous solution of $R7^+$ in the free base form is purified to a degree of purity to be determined by those having ordinary skill in the art, the solution can be brought into contact with a solution of one, or a mixture of more than one, $AN^-$ in an acid form, in an appropriate organic solvent, such as methyl ethyl ketone, methylene chloride, toluene, chloroform, or diethyl ether.

As a result, R7-FB will undergo an acid-base reaction with the free acid counter-ion and a $R7+/AN^-$ complex will accumulate in the organic phase.

3. Ion Exchange Method.

The R7-based complex containing a water soluble counter-ion, for example, fluoride-ion or chloride ion, can be prepared. The complex ($R7^+/F^-$) can be made, for example, by conventional cleavage and de-protection steps in peptide synthesis. It can also be made by adding an appropriate acid (e.g., HF, or HCl) to an aqueous solution of R7 free base. Those having ordinary skill in the art can select the R7:acid ratio to be employed.

A solution of one of the substances forming hydrophobic counter-ions or a mixture of more than one of such substances, for example, lithium, or sodium laurate ($C_{11}H_{23}COOMe^+$), or lauric acid, can be prepared in an appropriate organic solvent, such as chloroform, diethyl ether, toluene, or cyclohexane. In the formula of the laurate above, $Me^+$ is an alkali metal cation.

The aqueous solution of $R7^+/F^-$ complex can then be mixed with the organic solution of $C_{11}H_{23}COOLi^+$. Since $F^-$ and $Li^+$ prefer to be in the aqueous phase (due to their large heats of solvation), and the $R7^+$ cation and the laurate anion $C_{11}H_{23}COO^-$ are soluble in the organic phase, the corresponding "swap" or exchange of ions takes place. As a result, $R7^+$ having the hydrophobic counter-ion $C_{11}H_{23}COO^-$ coordinated to $R7^+$, accumulates in the organic phase and becomes organic solvent soluble, while the $Li^+$ $F^-$ salt accumulates in the aqueous phase.

Alternatively, the ion "swap" can be performed in an ion exchange column. According to this embodiment, the aqueous solution of R7 can be run through an ion exchange column containing an anion exchange resin, the column to be selected according to standard criteria known to those having ordinary skill in the art. An example of suitable anion exchange resin can be a phenolic resin with quaternized hydrophobic amino substituents. Other example of a suitable anion exchange resin can be a resin which includes $AN^-$ coordinated against the quaternized amino substituents. Such alternative anion exchange resin can be dissolved in a mixed alcohol-water solvent or a strong solvent, for example, dimethylsulfoxide.

If the anion exchange column is loaded with $AN^-$, emerging from the column will be the R7 coordinated with the $AN^-$ hydrophobic counter-ion. If the ion exchange column is loaded with hydroxide anion, $OH^-$, then this ion will swap for the counter-ion being present, for example the anion of trifluoroacetic acid. The R7 free base emerging from the column can then be contacted with an organic phase containing the organic acid and the organo-soluble $R7^+/AN^-$ complex will form.

4. The Method of Selective Precipitation.

According to this method, the aqueous solution of $R7^+/Cl^-$ complex can be prepared as described above. A solution of one of the substances forming hydrophobic counter-ions, for example, potassium laurate in an appropriate organic solvent can be prepared, as described above. The two solutions can be brought into a contact and silver hydroxide or silver oxide can be slowly added. Silver chloride, AgCl, will precipitate due to its extremely low solubility driving R7 into the organic phase where it will be coordinate with the $AN^-$ (the laurate anion) forming an organo-soluble $R7^+/AN^-$ complex, in this case, $R7^+$/laurate complex.

5. The Method of Volatilization of Counter-Ions.

According to this method, the aqueous solution of $R7^+/AN^-$ complex can be prepared. The $AN^-$ here is the anion of a volatile organic acid. One example of such a volatile organic acid is acetic acid, and $AN^-$ is accordingly the acetate-anion. A solution of the desired free acid, to ultimately become the hydrophobic counter-ion, for example, lauric acid, is prepared in an appropriate water-immiscible organic solvent. The two solutions can then be brought into contact and heated to a temperature sufficient to cause evaporation of the acetic acid, for example, about 100 deg. C. As acetic acid evaporates, it will drive the R7 into the organic phase to coordinate with the laurate ion.

The organo-soluble $R7^+/AN^-$ complex obtained by any method described above can be incorporated into a polymer layer coated on an implantable device, such as a stent. By way of example, the $R7^+/AN^-$ complex and a polymer forming a layer on a device can be dissolved in an organic solvent and the solution containing both the polymer and the $R7^+/AN^-$ complex can be applied by spraying or dipping techniques.

One variation of a method of volatilization of counter-ions can be used for facilitating the process of incorporating R7 into some polymer compositions. For example, it would be beneficial to blend R7 into an acrylic composition, then to apply the blend onto the stent. However, in the case of acrylic compositions which include carboxyl groups, such blending is often not feasible. For example, if the polymer contains units derived from acrylic acid, the composition is available in aqueous dispersion. When R7 is added to the dispersion, the stability of the dispersion is disturbed leading to coagulation.

The problem of coagulation can be overcome if R7 is used as a R7$^+$/AN$^-$ complex. One example of a suitable R7$^+$/AN$^-$ complex includes an acetate counter-ion AN$^-$. The R7$^+$/acetate complex can be prepared as described above. The complex is organo-soluble and a solution of R7$^+$/acetate complex in dimethylacetamide can be prepared, the solution containing between about 1% and about 10% by mass of R7$^+$/acetate complex.

The solution of R7$^+$/acetate complex can then be combined with a solution of poly(butylmethacrylate-co-acrylic acid) in a 70:30 (mass) mixture of dimethylacetamide and ethanol, the solution having between about 3% and about 5% (mass) of poly(butylmethacrylate-co-acrylic acid). The blend of the solutions of R7$^+$/acetate complex and of poly (butylmethacrylate-co-acrylic acid) can then be applied onto a stent as a "drug-polymer layer," and/or as a "topcoat layer," for example by spraying, to form a coating containing R7$^+$/acetate complex dispersed in poly(butylmethacrylate-co-acrylic acid).

This coating is then heated at a temperature of about 100° C. for about 2 hours leading to removal of acetic acid by volatilization and leaving R7 incorporated into poly(butylmethacrylate-co-acrylic acid). Ratios between the solutions of R7$^+$/acetate complex and of poly(butylmethacrylate-co-acrylic acid) are selected so as to have the ratio between R7 and poly(butylmethacrylate-co-acrylic acid) in the final coating between about 1:1 and 1:5, for example, 1:2.

Alternatively, a counter-ion AN$^-$ other than acetate can be used, as long as it can be volatilized at relatively low temperatures. One example of such suitable counter-ion is formate-anion HCOO$^-$ derived from formic acid HCOOH. Besides poly(butylmethacrylate-co-acrylic acid), other acrylic acid-containing polymers can be used, such as poly(ethylene-co-acrylic acid) (PEAA) having a general formula —[CH$_2$—CH$_2$]$_r$—[CH$_2$—CH(COOH)]$_s$—, where "r" and "s" are integers. PEAA is commercially distributed under a trade name PRIMACOR and can be obtained from Dow Plastics Co. of Midland, Mich. Other alternative suitable polymers include copolymers of maleic, methacrylic or itaconic acid with ethylene, other olefins, or other unsaturated monomers, for example, copolymers of acrylate esters, styrene and acrylic or methacrylic acid in a form of aqueous acrylic dispersion resins known under the trade name CARBOSET available from Goodrich Corp. of Charlotte, N.C.

B. Incorporating PArg into Stent Coatings by Entrapment of PArg on the Coating's Surface PArg such as R7 can be entrapped on the stent by one of the following methods:
(1) covalent conjugation of R7 to the polymer of the outermost layer of the stent coating;
(2) ionic coordination of R7 to the polymer coating on the stent; and
(3) "reversed" covalent conjugation.

After R7 has been entrapped by one of these methods, it can be coordinated with a counter-ion supplied by a polysaccharide or a combination of polysaccharides.

1. Covalent Conjugation of R7.

One method of incorporating PArg, such as R7, into the coating is by covalent attachment of the peptide to a functionalized surface of the coating followed by formation of an R7/polysaccharide complex. To covalently attach R7 to a stent, the stent can be coated with a polymer coating where the polymer of outermost layer of the coating, such as the reservoir layer or the optional topcoat layer, contains reactive groups, for example hydroxyl, glycidyl, amino, carboxyl, and/or other reactive groups, or a combination thereof. R7 can be chemically bonded to the polymer's backbone utilizing one or more of the pendant reactive groups.

A copolymer of ethylene and vinyl alcohol (EVOH) is one example of a polymer to which R7 can be chemically grafted. Poly(ethylene-co-vinyl alcohol) is also known under the trade name EVAL and is distributed commercially by Aldrich Chemical Company of Milwaukee, Wis. EVAL is also manufactured by EVAL Company of America of Lisle, Ill. EVAL has the general formula —[CH$_2$—CH$_2$]$_m$—[CH$_2$—CH(OH)]$_n$—, where m and n are integers. EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers.

Representative examples of other suitable polymers that can be used to fabricate a coating to which PArg (e.g., R7) can be chemically bonded include poly(butylmethacrylate-co-2-hydroxyethyl methacrylate), PBMA-PHEMA, poly (butylmethacrylate-co-acrylic acid) PBMA-PAA, poly(ethylene glycol) (PEG), EVAL-PEG blends, poly(ethylene-co-glycidyl methacrylate)(PEGMA), poly(ethyleneimine) (PEI), poly(ethylene-co-acrylic acid) (PEAA), and other copolymers having units derived from acrylic acid. The grafting of PArg to the polymer can be conducted directly on the stent or the grafting to the polymer can be achieved first, and the product of grafting is then applied on the stent.

Grafting R7 to EVAL is accomplished by esterification. First, EVAL can be halogenated by phosphorous trichloride PCl$_3$, phosphorous pentachloride PCl$_5$ thionyl chloride SOCl$_2$, or other appropriate halogenating agent, via EVAL's hydroxyl group. This process, a nucleophilic substitution S$_N$2 can be schematically illustrated according to reaction I:

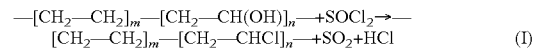

—[CH$_2$—CH$_2$]$_m$—[CH$_2$—CHCl]$_n$—+SO$_2$+HCl  (I)

The non-protonated non-terminal primary amino groups of R7 are protected by reaction II with 9-fluorenylmethyl chloroformate in aqueous dioxane as shown below. The 9-fluorenylmethyl chloroformate, also known as 9-fluorenylmethyloxycarbonylchloride or FMOC-chloride, has the formula

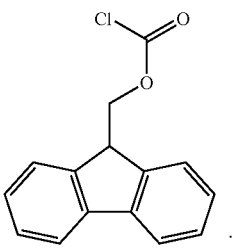

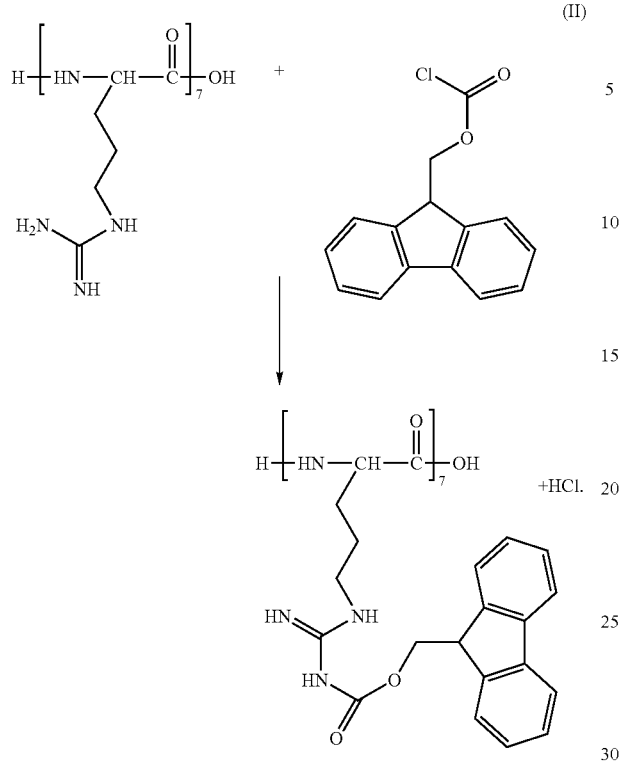

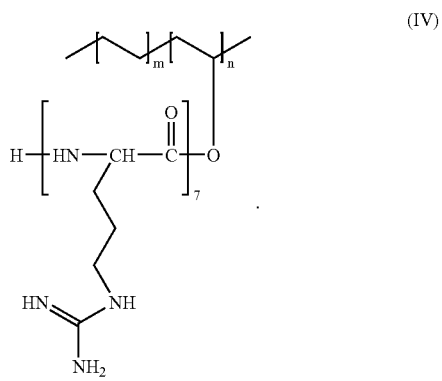

Finally, the product of reaction III is cleaved by 50% morpholine or other appropriate amine. As a result, the 9-fluorenylmethyl group is removed and R7 is tethered to EVAL by the ester bond, as shown by formula IV:

The reactions described above are conducted under the standard conditions which are known to those having ordinary skill in the art.

Alternatively, the amino groups of R7 can be protected using tBOC (di-tert-butyl dicarbonate) instead of FMOC. Next, the reaction of esterification is carried as illustrated by scheme III. In the reaction of esterification, the carboxyl group of the protected molecule of R7 is reacted with the halogenated EVAL obtained in reaction (I):

Alternatively, the protected R7 can be conjugated to EVAL by the reaction of direct esterification, which can be carried in the presence of 1,3-dicyclohexylcarbodiimide (DCC). DCC activates the carboxyl group of R7, thus facilitating the esterification reaction of nucleophilic substitution (V):

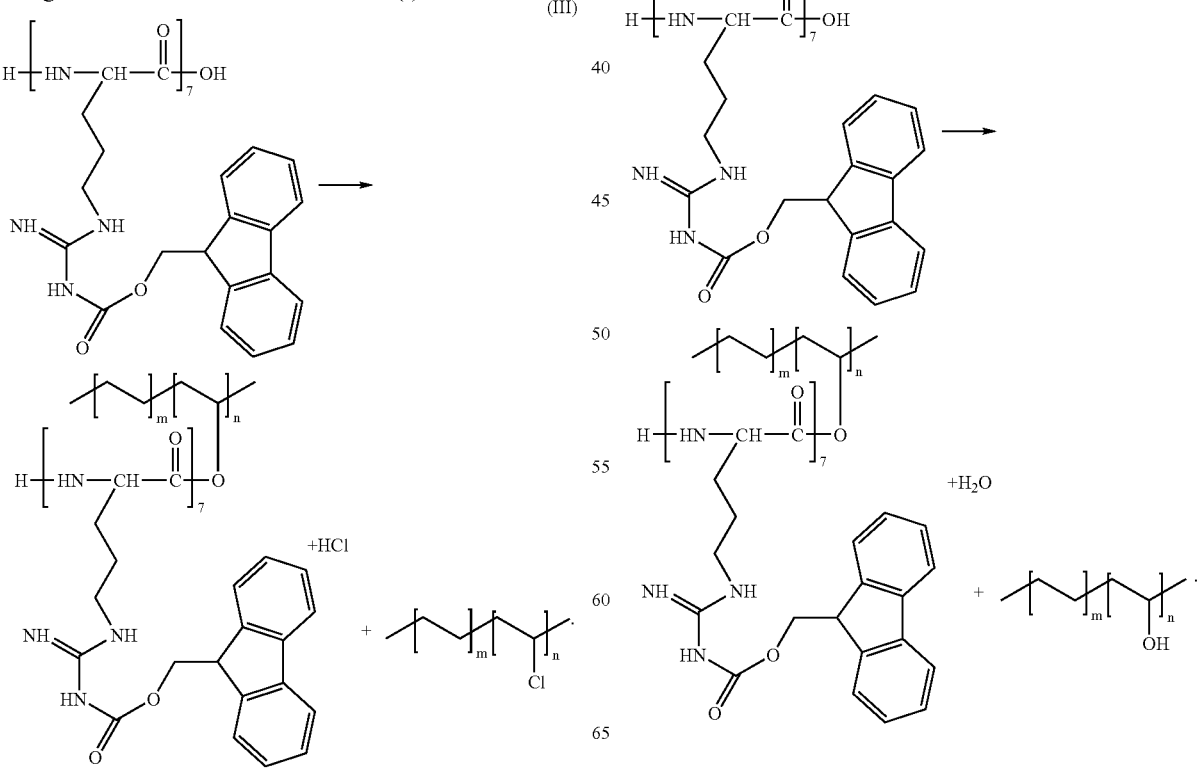

Reaction V is conducted under standard conditions known to those having ordinary skill in the art. An insoluble substance, N,N-dicyclohexylurea having the formula

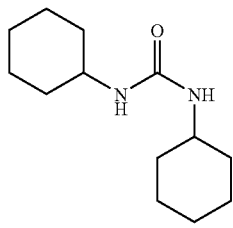

is a by-product of the reaction (V). Finally, the R7-EVAL conjugate, the product of reaction V, is de-protected by the same reaction with morpholine or another appropriate amine.

In accordance with yet another embodiment, the reaction of direct esterification can be carried out in the presence of dimethylaminopyridine (DMAP).

Due to the presence of a very strongly basic guanidinium fragment and of the acidic carboxyl group, R7, in the non-conjugated to EVAL form, is a zwitterion—a substance having dual acid-base nature. When R7 is esterified, the hydroxyl fragment of the carboxyl group (and the negative charge it carries) is removed. As a result, the R7-EVAL conjugate is a cation. This cation is designated as POL-R7$^+$, where POL is a polymer to which R7 is conjugated, in this case, EVAL. The positive charge is mainly concentrated on the imino nitrogen of R7 (NH=fragments).

After the POL-R7$^+$ cation is formed, it can be brought into contact with a naturally occurring anionic polysaccharide, or a blend thereof. One appropriate polysaccharide is heparin or a derivative thereof (Hep$^-$) such as heparin salts and heparinoids. Examples of other suitable anionic polysaccharides include dermatan sulfate, keratan sulfate, chondroitin sulfate, hyaluronic acid and hyaluronates. The Hep$^-$ coordinates around POL-R7$^+$, thus entrapping R7 on the stent surface by forming a complex POL-R7$^+$/Hep$^-$ as shown by reaction (VI):

$$POL\text{-}R7^+ + Hep^- \rightarrow POL\text{-}R7^+/Hep^- \qquad (VI)$$

According to another embodiment, R7 can be grafted to a surface containing amino groups, for example, when the outermost layer of the stent coating includes PEI. PEI has a general formula $NH_2-[CH_2-CH_2-N(CH_2-CH_2-NH_2)]_p-[CH_2-CH_2-NH]_q-$, where "p" and "q" are integers. PEI is commercially manufactured and can be obtained from Economy Products Co. of Houston, Tex.

In order to graft R7 to PEI, the primary amino groups of R7 are first protected by FMOC or tBOC, as shown by reaction II. Next, the protected R7 is reacted with PEI. The amino groups of PEI react with the carboxyl groups of the protected R7 to form amide derivatives. One example of a possible path of such reaction can be illustrated by reaction VII, which can be carried in the presence of the equimolar or greater amount of 1-ethyl-3(3-dimethylaminopropyl) carbodiimide, (EDC), having the formula $CH_3-CH_2-N=C=N-CH_2-CH_2-CH_2-N(CH_3)_2$. EDC is manufactured by Pierce Corp. of Rockford, Ill.

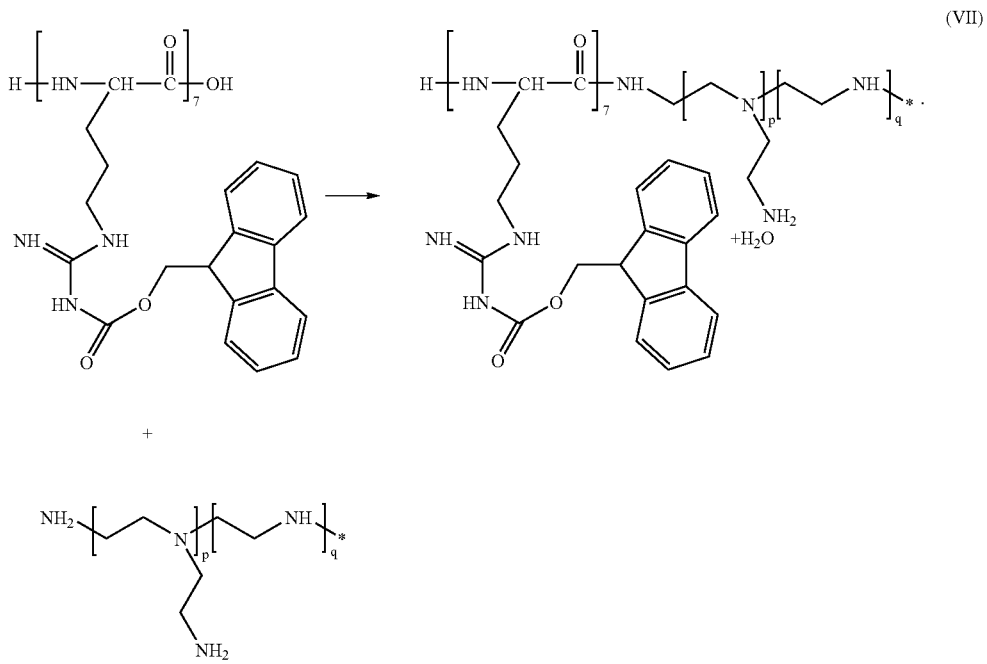

(VII)

Finally, the product of reaction (VII) is cleaved by 50% morpholine or other appropriate amine. As a result, the 9-fluorenylmethyl group is removed and R7 is tethered to PEI by the amide bond, as shown by the formula VIII:

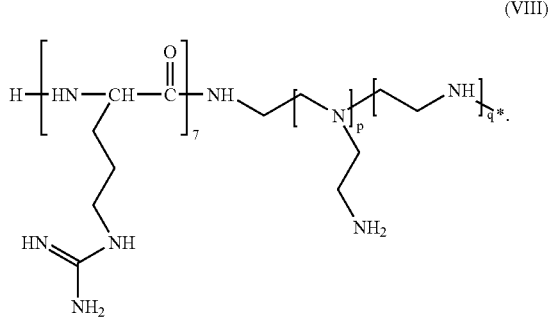

(VIII)

The reactions described above are conducted under the standard conditions which are known to those having ordinary skill in the art.

Again, the PEI-R7 conjugate of formula VIII is a POL-R7$^+$ cation (where POL is PEI). This cation can be brought in contact with one of the anionic polysaccharides described above, or a blend thereof, for example, Hep$^-$. As a result, R7 is entrapped on the stent surface by forming a complex POL-R7$^+$/Hep$^-$ as shown by reaction (VI).

According to yet another embodiment, R7 can be grafted to a surface containing carboxyl groups, for example, when the outermost layer of the stent coating includes PEAA. PEAA can react with unprotected R7, where carboxyl groups of PEAA and amino groups of R7 form an amide. One possible path of reaction, which is carried out in the presence of EDC or DCC, can be illustrated by reaction (IX):

de-protecting these groups. The PEAA-R7 conjugate which is a product of reaction IX is a POL-R7$^+$ cation (POL being PEAA). This cation can be brought in contact with one of the anionic polysaccharides described above, or a blend thereof, for example, Hep$^-$. As a result, R7 is entrapped on the stent surface by forming a complex POL-R7$^+$/Hep$^-$ as shown by reaction VI.

Alternatively, instead of using the surface containing the carboxyl groups, R7 can be grafted to the surface containing anhydride groups. Those having ordinary skill in the art will realize that the chemistry of R7-anhydride grafting would be similar to the reaction (IX), and will choose the appropriate conditions for accomplishing such grafting.

2. Ionic Coordination of R7.

Instead of covalently bonding R7 to carboxyl-containing polymers present in the outermost layer of the stent coating, R7 can be entrapped by forming an ionic complex with the carboxylated stent surface. The carboxyl groups are provided by acid-type polymers forming the stent coating, for example by PEAA.

Even R7 having its carboxyl group intact carries some positive charge and is cationic. It can be blended with PEAA and the pH of the blend can be raised by adding some base such as KOH. Under such alkaline conditions, PEAA will be ionized by de-protonization and will become anionic. Schematically, this can be illustrated by reaction (X):

$$—[CH_2—CH_2]_r—[CH_2—CH(COOH)]_s—+[OH^-] \rightarrow —[CH_2—CH_2]_r—[CH_2—CH(COO^-)]_s— \quad (X)$$

The anion (X) can be brought into contact with R7 causing coordination of the anion around R7. Such process has to be carried out under mild conditions so as to avoid the formation of the amide demonstrated by reaction (IX).

The product of ionic coordination of anion X around R7 will still be somewhat cationic because the positive charge on R7 is expected to be only partially offset by the negative

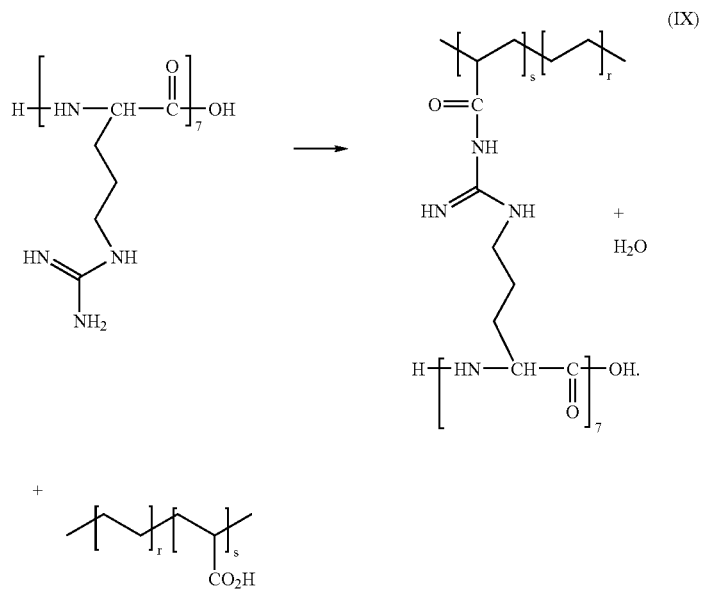

(IX)

Those having ordinary skill in the art will select the conditions suitable for carrying out reaction IX, such as protecting amino groups R7 with FMOC and ultimately charge on anion (X). Thus, the product of ionic coordination will be POL-R7$^+$ cation (POL being PEAA). This cation can be brought in contact with one of the anionic polysaccharides described above, or a blend thereof, for instance, Hep⁻. As a result, R7 is entrapped on the stent surface by forming a complex POL-R7⁺/Hep⁻ as shown by reaction (VI), and the final coating will contain both anti-thrombotic and anti-restenotic components.

A variation of this method would allow entrapment of R7 on a coated stent where the coating is polyanionic. One way of creating a polyanionic coating is to include in the outermost layer of the coating an anionic polysaccharide, an anionic hydrogel or a mixture thereof, for example, heparin, hyaluronic acid, sulfated poly(ethylene glycol), sulfonated poly(ethylene glycol), carboxylated poly(ethylene glycol), or a mixture of anionic polysaccharides and hydrogels. Heparin can be applied onto the stent by techniques known to those having ordinary skill in the art. For example, a stent having a CARMEDA heparin coating or a TRILLIUM heparin coating can be used. Stents coated with CARMEDA or TRILLIUM coatings are manufactured by Cordis Corp., a Johnson & Johnson company of Miami Lakes, Fla., and BioInteractions, Ltd. of Reading, England, respectively.

The process of incorporating R7 on a heparin-coated stent can be demonstrated by the following example. Stainless steel coupons were coated with the BioInteractions' heparin TRILLIUM coating. The coupon was cut into about 1 cm width and about 3 cm length and weighed. The total heparin coated surface area was about 6 cm². About 0.1 gram of R7 was dissolved in about 1 gram of a 1:1 by weight water/acetone mixture. The coupon was immersed into R7 solution at 37° C. for about 1.5 hrs and dried at 65° C. for about 1 hr. Average loading for two coupons was about 330 μg/cm². The release rate was studied in PBS buffer (PH=7.4) at 37° C.

R7 content was semi-quantified with Bradford dye assay, which is commonly used to determine the total concentration of the peptide in the solution. The procedure is based on the formation of a complex between the dye and the peptide in the solution. The dye-peptide complex causes a shift in the wavelength at which the absorption of the dye reaches maximum from about 485 to 595 nm. The amount of peptide in the complex is proportional to the total peptide present.

A UV spectrometer (Cary 3E) was used in the experiment. R7 concentration was quantified by comparison with standard R7 curve. Within first 30 minutes, 80% of R7 eluted into the media, the remaining 22% continued eluting for 3 days.

According to another embodiment, the heparin-coated stent can be placed at a diseased site in a blood vessel in the usual manner. Due to the anionic nature of heparin, the stent coating will carry a negative charge. R7 is then administered systemically, for example, intravenously or orally. R7 will be carried through the circulatory system and when R7 approaches the stent, some of positively charged R7 will coordinate around heparin to form a R7⁺/Hep⁻ complex, thus trapping R7. After untrapped R7 is cleared from the circulatory system, trapped R7 will still persist for some time.

3. "Reversed" Covalent Conjugation.

According to this method, the order of steps discussed in the method of covalent conjugation above is reversed. In one embodiment, a polysaccharide such as heparin can be grafted to a surface containing amino groups, for example, when the outermost layer of the stent coating includes PEI. To graft, PEI is reacted with heparin utilizing amino groups of PEI and carboxyl groups of heparin. An amide bond is formed as in reaction VII, except that here instead of carboxyl groups of R7, carboxyl groups of heparin take part in the formation of the amide. As a result, the POL-Hep⁻ anion is obtained, where POL is PEI and POL is covalently bonded to Hep⁻ via the amide bond.

This POL-Hep⁻ anion can be brought in contact with R7. As a result, R7 is entrapped on the stent surface by forming a complex POL-Hep⁻/R7⁺. It should be noted that the POL-Hep⁻/R7⁺ complex is a mirror image of the complex shown by reaction VI, where the positions of Hep⁻ and R7⁺ are reversed.

Alternatively, PEI can be reacted with a heparin derivative terminated with an aldehyde group, —C(O)H. Such reaction, conducted under the conditions to be selected by those having ordinary skill in the art will produce the same POL-Hep⁻ product. Yet another alternative is to use in the outermost layer of the stent coating the polymer having aldehyde groups instead of PEI. The aldehyde groups will react with amino groups of heparin to yield the same POL-Hep⁻ product. An amino-derivative of heparin R7 can also be used as a source of amino groups to be reacted with the aldehyde groups. Heparin products having aldehyde or amino moieties can be obtained from Celsus Laboratories, Inc. of Cincinnati, Ohio. The POL-Hep⁻ product can be brought into contact with POL-Hep⁻ to form the same POL-Hep⁻/R7⁺ complex as described above.

C. Incorporating PArg into Stent Coatings by Using Ion Exchange Microspheres

In order to incorporate PArg into a stent coating, ion exchange microspheres can be fabricated, followed by absorbing PArg into the microspheres and by embedding the microspheres into the polymer of the reservoir coating layer and/or a topcoat layer.

Ion exchange microspheres or beads can be fabricated by suspension polymerization. For example, styrene and divinyl benzene can be co-polymerized in a suspension containing mineral oil, sodium polyacrylates as a dispersant and in the presence of a peroxide initiator of radical polymerization. In addition, ion exchange microspheres or beads can be fabricated by emulsion polymerization of at least one neutral monomer, at least one anionic monomer or at least one cross-linking monomer. The ionic functionality can be also added after the microsphere is formed.

Examples of neutral monomers that can be used in the process of synthesis of the microspheres by suspension or emulsion polymerization include acrylic or vinyl monomers, such as acrylamide $CH_2$=CH—$CONH_2$, methyl methacrylate $CH_2$=C($CH_3$)—$COOCH_3$, ethyl methacrylate $CH_2$=C($CH_3$)—$COOCH_2CH_3$, butyl methacrylate $CH_2$=C($CH_3$)—$COOC_4H_9$, 2-hydroxyethyl methacrylate $CH_2$=C($CH_3$)—$COOCH_2$—$CH_2OH$, styrene $C_6H_5$—CH=$CH_2$, and PEG terminated on one terminus with either an acrylate or a methacrylate group (PEG-acrylate and PEG-methacrylate, respectively).

Examples of anionic monomers that can be used include acrylic or vinyl monomers having acid moieties, e.g., acrylic acid $CH_2$=CH—COOH, methacrylic acid $CH_2$=C($CH_3$)—COOH, ethyl acrylic acid $CH_2$=C($C_2H_5$)—COOH, propyl acrylic acid $CH_2$=C($C_3H_7$)—COOH, and carboxylated or sulfonated styrenes.

Examples of cross-linking monomers that can be used include acrylic or vinyl compounds, for example, propyleneglycol dimethacrylate $CH_2$=CH—COO—CH($CH_3$)—$CH_2$—OOC—CH=$CH_2$, divinyl benzene $CH_2$=CH—$C_6H_4$—CH=$CH_2$, N,N'-methylenebisacrylamide ($CH_2$=CH—CO—NH$)_2CH_2$, trimethylolpropane triacrylate ($CH_2$=CH—COOC$)_3$C—$CH_2$—$CH_3$, propyleneglycol diacrylate $CH_2$=CH—COO—CH($CH_3$)—$CH_2$—OOC—

CH=CH$_2$, and PEG terminated on each terminus with either an acrylate or methacrylate group (PEG-diacrylate and PEG-dimethacrylate, respectively).

The reaction of emulsion copolymerization is carried out in the presence of a typical initiator of radical polymerization such as benzophenone, hydroxycyclohexyl phenyl ketone, a blend of ammonium persulfate with N,N,N',N'-tetramethylethylenediamine, benzoyl peroxide or cumyl peroxide. The organic phase is selected from one or more of mineral oil, cyclohexane, cycloheptane, cyclooctane, octane, heptane, hexane, methylene chloride, chloroform or decalin. Those having ordinary skill in the art will select appropriate conditions under which the process of emulsion copolymerization is carried as well as a suitable emulsifier, for example one of TWEEN, SPAN, BRIJ, MYRJ, PLURONIC, TETRONIC or IGEPAL families.

TWEEN is a trade name of a family of polyoxyethelene-sorbitan monooleates. SPAN is a trade name of a family of sorbitan monostearates. BRIJ is a trade name of a family of polyoxyethylene ethers. TWEEN, SPAN, BRIJ are available from ICI Americas, Inc. of Bridgewater, N.J. MYRJ is a trade name of a family of propylene glycol monostearates and is available from Uniqema Corp. of New Castle, Del. PLURONIC is a trade name of poly(ethylene oxide-co-propylene oxide). TETRONIC is a trade name of a family of nonionic tetrafunctional block-copolymer surfactants. PLURONIC and TETRONIC are available from BASF Corp. of Parsippany, N.J. IGEPAL is a trade name of a family of amphoteric ethers and is available from Rhone-Poulenc, Inc. of Cranbury, N.J.

The microspheres which are a product copolymerization can have a diameter within a range of between about 0.2 and 10 micrometers. For example, microspheres having diameter between about 0.1 and 5 micrometers can be used. Following the fabrication of the microspheres, PArg such as R7, can be incorporated into the microspheres.

Furthermore, commercially manufactured microspheres, for example, microspheres made of a copolymer of styrene and divinyl benzene, can be used for incorporating PArg. Commercially manufactured microspheres are available from Advanced Polymer Systems, Inc. of Redwood City, Calif. or from Dow Chemical Co. of Midland, Mich.

The methods of incorporating R7 into the microspheres to form a microsphere-R7 complex may vary depending on the form of R7 used. For example, if R7 is in a free base form, R7 can be blended with the microspheres in the free acid form. Since the microspheres are porous, they will swell upon exposure to water and R7 in the free base form will be absorbed into the microspheres. If R7 already has counter-ions (e.g., acetate or trifluoroacetate anions) coordinated around R7, the microspheres can be mixed with R7 in aqueous solution followed by the process of dialysis described above. Alternatively, the microspheres can be first neutralized to the sodium salt, then placed into a column similar to a chromatographic column. An excess amount of R7$^+$/AN$^-$, for example, R7$^+$/Cl$^-$ can then be passed through the column causing the exchange process and trapping R7 inside the microspheres.

The microspheres loaded with R7 can optionally be dried and then mixed with a polymer solution which is used to fabricate the coating layer, e.g., the reservoir layer and/or a top coat layer. When the microspheres contact the organic solvent of the polymer solution, for example, dimethylacetamide, the water will be extracted from the microspheres causing their collapse, but R7 will remain incorporated into the polymer. The microspheres can also be first dehydrated with ethanol or lyophilized.

D. Incorporating PArg into Stent Coatings by Using Hydrogels

In order to incorporate PArg such as R7 into a stent coating, a hydrogel coating can be fabricated, followed by absorbing R7 into the hydrogel coating. After R7 has been absorbed, a topcoat layer can be optionally applied. If desired, this method can be used also for other polycationic peptides described above, and for any cationic therapeutically active material.

A primer layer can be optionally applied on the stent. Examples of polymers suitable for the optional primer layer include EVAL, PEAA or poly(butylmethacrylate) (PBMA). Alternatively, the primer layer can be made of pyrolytic carbon coating having abstractable hydrogen (diamond-like coating having both sp$^2$ and sp$^3$ carbon atoms and applied by plasma-assisted chemical vapor deposition). One example of a suitable diamond-like carbon coating is DYLYN which can be obtained from ART, Inc. of Buffalo, N.Y.

A hydrophilic UV-curable anionic coating can be applied forming a hydrogel. As a general rule, the degree of hydrophilicity of a polymer is proportional to the value of the Hildebrand solubility parameter δ. Polymers that are very hydrophilic may have a high δ value. A polymer that is sufficiently hydrophilic for use in the hydrophilic UV-curable anionic coating of the present invention can have a solubility parameter higher than about 11 (cal/cm$^3$)$^{1/2}$.

The hydrophilic UV-curable anionic coating can have solid contents, i.e., non-volatile compounds, of between about 0.2% and about 25% by weight. The non-volatile compounds can include acrylate, methacrylate, allyl or vinyl monomers and/or oligomers, some of which may have non-ionic hydrophilic groups, oligoacrylate groups to provide high cross-linking, and/or anionic groups.

The non-ionic hydrophilic groups can include PEG-acrylate groups, PEG-methacrylate groups, hydroxymethyl methacrylate groups, and/or acrylamido groups. The oligoacrylate groups may include trimethylolpropane triacrylate groups and/or bis-acrylamido groups. The anionic groups can include carboxylates, sulfates, and/or phosphates. Hydrophilic polymers such as PEG, poly(vinyl pyrrolidone), hyaluronic acid, carboxymethyl cellulose, dextran sulfate, chondroitan sulfate, and/or heparin can also be optionally added to the formulation of the hydrophilic UV-curable anionic coating.

The formulation may also optionally contain up to 10% photoinitiator, based on the total mass of the non-volatile compounds. Examples of suitable photoinitiators include benzophenone and/or hydroxycyclohexyl phenyl ketone. The volatile compounds of the formulation include water, lower alcohols, and/or ketones, or mixtures thereof. Optionally, co-solvents, such as dimethylformamide, dimethylsulfoxide, and/or dimethylacetamide can be also added.

The formulation described above can be applied by any acceptable method, such as spraying, and then can be dried and UV-cured. R7 can then be applied onto the cured hydrogel followed by application of an optional topcoat. Acceptable polymers that can be used for the fabrication of the topcoat include PBMA, EVAL, PEAA, poly(vinylidene fluoride) and derivatives thereof.

The process of fabrication of the hydrophilic UV-curable anionic coating forming a hydrogel can be illustrated by the following example. A primer layer was first formed. A 3% (by mass) solution of poly(butylmethacrylate) in a blend of solvents (xylene, acetone and TECHSPRAY) was applied in a series of 10-second passes to deposit 10 μg of coating per spray pass on a 13-mm TETRA stent (available from Guidant Corporation). Between the spray passes, the stent was dried for about 10 seconds using flowing air with a temperature of about 60° C. Seven spray passes were applied to form a 70 µg primer layer, followed by baking the primer layer at about 70° C. for approximately two hours. The hydrogel formulation for making the drug-polymer layer was then prepared as shown in Table 1.

TABLE 1

A Formulation for Preparing a Hydrophilic UV-Curable Anionic Hydrogel-Forming Coating

| Component | Amount, grams | Comment |
| --- | --- | --- |
| 3% solution of PAA in butyl alcohol | 18.0 | Polymer |
| 3% solution of PAA in isopropyl alcohol | 8.7 | Polymer |
| Photomer 4158 | 0.4 | Cross-linking monomer available from Cognis Corp. of Cincinnati, Ohio |
| PEG-acrylate | 0.05 | Monomer available from Sigma-Aldrich Corp. of St. Louis, Missouri |
| Benzophenone | 0.02 | Photoinitiator available from Sigma-Aldrich Corp. of St. Louis, Missouri |
| Hydroxycyclohexyl phenyl ketone | 0.02 | Photoinitiator available from Sigma-Aldrich Corp. of St. Louis, Missouri |
| Methyl ethyl ketone | 15.0 | Solvent |
| n-Butanol | 18.0 | Solvent |
| i-Propanol | 12.6 | Solvent |

The formulation described above was sprayed onto the primer layer and dried in the same way as described for the primer layer. About 200 µg of dry coating was formed. The coating was then exposed to UV-radiation for curing. 12 mW medium pressure mercury UV-lamp was used and the time of exposure was about 5 minutes. As a result, the hydrophilic anionic hydrogel drug-polymer layer was formed.

R7 was dissolved in 50% (mass) aqueous ethanol to obtain about 1% mass concentration of R7. Ammonium hydroxide was added to the R7 solution and the pH of the solution was raised to about 10. The solution was then sprayed onto the cured hydrogel drug-polymer layer in a series of passes until about 200 µg of dry R7 was deposited. In view of high hydrophilicity of the drug-polymer layer, R7 was absorbed and the stent was then baked at 70° C. for two hours. Finally, the stent coating was completed by spraying a topcoat. PBMA was used as a polymer forming the topcoat and about 100 µg of dry PBMA was deposited.

E. Incorporating PArg into Stent Coatings by Using Polyelectrolytes

Polyelectrolytes are molecules with multiple charged sites. The peptides described above, such as poly(L-arginine), poly(D-arginine), poly(D,L-arginine), poly(L-lysine), poly(D-lysine), poly(δ-guanidino-α-aminobutyric acid), racemic mixtures of poly(L-arginine) and poly(D-arginine), and chitosan are polycations because they carry multiple positively charged groups. If a polycation is brought into contact with a polyanion, they will bond via ionic bonding.

In order to incorporate PArg, such as R7, into a stent coating, the polyelectrolyte properties of R7 can be exploited. A polyelectrolyte, e.g., cationic R7, or a mixture of polycationic polyelectrolytes, can be applied onto the stent and optionally dried, then a polyanionic electrolyte, or a mixture of polyanionic polyelectrolytes, can be applied. Examples of suitable polyanionic electrolytes include oligonucleotides, RNA, chondroitan sulfate, dextran sulfate, heparin and its derivatives, hyaluronic acid, hyaluronates, carboxymethyl cellulose, poly(acrylic acid), poly(methacrylic acid), poly(ethyl acrylic acid), poly(propyl acrylic acid), PEAA, and poly(ethylene-co-methacrylic acid). In one embodiment, a process of applying alternating polyelectrolyte layers can be employed and repeated any suitable number of times. For example, a stent can be coated with a layer of PEI. The thickness of the PEI layer can be between about 0.05 and about 2.0 micrometers. Polyamino compounds, for example, poly(allyl amine) can be used in the alternative. The stent is dried and an aqueous solution of an anionic polysaccharide, such as heparin, is applied, for example, by spraying, and optionally dried, to form a heparin layer having the thickness of between about 0.05 and about 2.0 micrometers. Heparin can be either in an acid form or in an ionized form.

A layer of a polycationic peptide can then be applied, for example, R7 or other peptide selected from those described above, to form a layer having the thickness of between about 0.05 and about 2.0 micrometers. R7 can be either in a free base form or in an ionized form.

Optionally, a binder material can be included in either or both polyelectrolyte coating solutions to modify mechanical, physical or pharmacological properties of the coating. Examples of suitable binder materials include poly(vinyl alcohol), EVAL, PVP, hydroxyethyl cellulose and cellulose acetate. Each polyelectrolyte can be in a 100% water solution, or, optionally, the solution can contain some water miscible co-solvents, such as dimethyl formamide, dimethyl acetoamide, dimethyl sulfoxide, acetone, and tethrahydrofurane.

The process of applying of alternating heparin and R7 layers is then repeated any suitable number of times, for example, between 2 and 100 times, until the desired thickness of the coating has been achieved. Alternatively, the polycationic polyelectrolyte forming the second and each successive layer can be one of the polycationic polyelectrolytes other than R7 as described above, or a mixture of such polycationic polyelectrolytes. Similarly, the polyanionic polyelectrolyte can be different polyanionic polyelectrolytes for each of the successive layers.

As a result of the above-described procedure, a multilayer structure is built, where the layers of the polycationic and polyanionic polyelectrolytes alternate, and the layers of R7 and heparin interdiffuse and bind to one another. The binding can be ionic or, if R7 is in the free base form and heparin in the acid form, via acid-base neutralization. Upon exposure to blood, or other body fluids, both R7 and heparin will be slowly released from the stent's surface and will be carried to the diseased site in the body, providing enhanced therapeutic effect.

A variation of the polyelectrolyte method described above can be illustrated by the following example. The conventional EFD coater can be modified to have dual barrels. One barrel can contain R7 and EVAL dissolved in the mixture of about 30% by mass of methanol and about 70% by mass of dimethylacetamide. The other barrel can contain a solution of heparin in EVAL, the solution comprised of about 0.1 g of sodium heparin, about 1 ml of formamide, about 3 g of 5% EVAL in dimethylacetamide, and about 1 gram of methanol. A layer of R7/EVAL can be spray coated followed by spraying a layer of sodium heparin/EVAL. The procedure of applying alternating layers of R7/EVAL and sodium heparin/EVAL can be repeated until the desired coating weight is reached, for example, 600 µg for a 13 mm TETRA stent. Optionally, a topcoat of EVAL or PBMA polymer can be finally applied.

In accordance to one embodiment of the invention, a therapeutic substance or active agent can be incorporated into the described embodiments of the coating. The active agent could be for inhibiting the activity of vascular smooth muscle cells; more particularly the agent can be directed at inhibiting abnormal or inappropriate migration and/or proliferation of smooth muscle cells to inhibit restenosis. Generally speaking, the active agent can include any substance capable of exerting a therapeutic or prophylactic effect in the practice of the present invention. Examples of the drugs which are usable include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, estradiol, clobetasol, dexamethasone, and structural analogs or functional derivatives thereof.

The coatings and methods of the present invention have been described in conjunction with a stent. The stent can be used in any part of the vascular system, including neurological, carotid, coronary, renal, aortic, iliac, femoral or any other peripheral vascular site. The stent can be balloon-expandable or self-expandable. The are no limitations on the size of the stent, its length, diameter, strut thickness or pattern. The use of the coating is, however, not limited to stents and the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A therapeutic composition, comprising a polycationic peptide and a hydrophobic counter-ion coordinated with the polycationic peptide.

2. The composition of claim 1, wherein the polycationic peptide includes a component selected from a group consisting of poly(L-arginine), poly(D-arginine), poly(D,L-arginine), poly(L-lysine), poly(D-lysine), poly(δ-guanidino-α-aminobutyric acid), and a mixture of poly(L-arginine) and poly(D-arginine).

3. The composition of claim 1, wherein the hydrophobic counter-ion includes a component derived from saturated fatty acids, unsaturated fatty acids, phospholipids, sulfates, aromatic compounds or hydrophobic anionic compounds.

4. The composition of claim 3, wherein the saturated fatty acids include a component selected from a group consisting of formic acid, acetic acid, propionic acid, butyric acid, valeric acid, caproic acid, heptanoic acid, caprylic acid, nonanoic acid, capric acid, hendecanoic acid, lauric acid, myristic acid, palmitic acid, stearic acid, arachidic acid, and any salt thereof.

5. The composition of claim 3, wherein the unsaturated fatty acids include a component selected from a group consisting of palmitoleic acid, oleic acid, linoleic acid, arachidonic acid, and any salt thereof.

6. The composition of claim 3, where the phoshpolipids include a component selected from a group consisting of phosphatidic acids, phosphatidylinositol, phosphatidylglycerol diphosphatidylglycerol, and any salt thereof.

7. The composition of claim 3, wherein the sulfates include sodium dodecyl sulfate.

8. The composition of claim 3, wherein the aromatic compounds include a component selected from a group consisting of benzoic acid, aromatic sulfonates, salicylic acid, acetylsalicylic acid, and derivatives thereof.

9. The composition of claim 3, wherein the hydrophobic anionic compounds include a component selected from a group consisting of statins, retinoic acid and retinoids.

10. A method for making a polycationic peptide soluble in an organic solvent, comprising preparing a complex of the peptide with a hydrophobic counter-ion.

11. The method of claim 10, wherein the complex is prepared by a method selected from a group consisting of a free base method, a dialysis method, an ion exchange method, a selective precipitation method, and a volatilization method.

12. The method of claim 10, wherein the polycationic peptide includes a component selected from a group consisting of poly(L-arginine), poly(D-arginine), poly(D,L- arginine), poly(L-lysine), poly(D-lysine), poly(δ-guanidino-α-aminobutyric acid), and a mixture of poly(L-arginine) and poly(D-arginine).

13. The method of claim 10, wherein the hydrophobic counter-ion includes a component derived from saturated fatty acids, unsaturated fatty acids, phospholipids, sulfates, aromatic compounds, or from hydrophobic anionic compounds.

14. The method of claim 13, wherein the saturated fatty acids include a component selected from a group consisting of formic acid, acetic acid, propionic acid, butyric acid, valeric acid, caproic acid, heptanoic acid, caprylic acid, nonanoic acid, capric acid, hendecanoic acid, lauric acid, myristic acid, palmitic acid, stearic acid, arachidic acid, and any salt thereof.

15. The method of claim 13, wherein the unsaturated fatty acids include a component selected from a group consisting of palmitoleic acid, oleic acid, linoleic acid, arachidonic acid, and any salt thereof.

16. The method of claim 13, where the phoshpolipids include a component selected from a group consisting of phosphatidic acids, phosphatidylinositol, phosphatidylglycerol diphosphatidylglycerol, and any salt thereof.

17. The method of claim 13, wherein the sulfates include sodium dodecyl sulfate.

18. The method of claim 13, wherein the aromatic compounds include a component selected from a group consisting of benzoic acid, aromatic sulfonates, salicylic acid, acetylsalicylic acid, and derivatives thereof.

19. The method of claim 13, wherein hydrophobic anionic compounds include a component selected from a group consisting of statins, retinoic acid and retinoids.

20. A coating for an implantable medical device, the coating comprising a polycationic peptide and a hydrophobic counter-ion coordinated with the polycationic peptide.

21. The coating of claim 20, wherein, the medical device comprises a stent.

22. The coating of claim 20, wherein the polycationic peptide includes a component selected from a group consisting of poly(L-arginine), poly(D-arginine), poly(D,L-arginine), poly(L-lysine), poly(D-lysine), poly(δ-guanidino-α-aminobutyric acid), and a mixture of poly(L-arginine) and poly(D-arginine).

23. The coating of claim 20, wherein the hydrophobic counter-ion includes a component derived from saturated fatty acids, unsaturated fatty acids, phospholipids, sulfates, aromatic compounds, or from hydrophobic anionic compounds.

24. The coating of claim 23, wherein the saturated fatty acids include a component selected from a group consisting of formic acid, acetic acid, propionic acid, butyric acid, valeric acid, caproic acid, heptanoic acid, caprylic acid, nonanoic acid, capric acid, hendecanoic acid, lauric acid, myristic acid, palmitic acid, stearic acid, arachidic acid and any salt thereof.

25. The coating of claim 23, wherein the unsaturated fatty include a component selected from a group consisting of palmitoleic acid, oleic acid, linoleic acid, arachidonic acid, and any salt thereof.

26. The coating of claim 23, where the phoshpolipids include a component selected from a group consisting of phosphatidic acids, phosphatidylinositol, phosphatidylglycerol diphosphatidylglycerol, and any salt thereof.

27. The coating of claim 23, wherein the sulfates include sodium dodecyl sulfate.

28. The coating of claim 23, wherein the aromatic compounds include a component selected from a group consisting of benzoic acid, aromatic sulfonates, salicylic acid, acetylsalicylic acid, and derivatives thereof.

29. The coating of claim 23, wherein hydrophobic anionic compounds include a component selected from a group consisting of statins, retinoic acid and retinoids.

* * * * *